US010617975B2

(12) United States Patent
Skudas et al.

(10) Patent No.: US 10,617,975 B2
(45) Date of Patent: Apr. 14, 2020

(54) TARGET MOLECULE CAPTURE FROM CRUDE SOLUTIONS

(71) Applicant: MERCK PATENT GMBH, Darmstadt (DE)

(72) Inventors: Romas Skudas, Mainz (DE); Klaus Adrian, Grosswallstadt (DE); Bianca Edelmann, Pfungstadt (DE); Matthias Joehnck, Muehltal (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/536,324

(22) PCT Filed: Nov. 18, 2015

(86) PCT No.: PCT/EP2015/002306
§ 371 (c)(1),
(2) Date: Jun. 15, 2017

(87) PCT Pub. No.: WO2016/096071
PCT Pub. Date: Jun. 23, 2016

(65) Prior Publication Data
US 2017/0340989 A1 Nov. 30, 2017

(30) Foreign Application Priority Data
Dec. 15, 2014 (EP) .................... 14004224

(51) Int. Cl.
*B01D 15/32* (2006.01)
*C07K 1/20* (2006.01)
*B01D 15/26* (2006.01)
*C04B 103/00* (2006.01)

(52) U.S. Cl.
CPC ......... *B01D 15/327* (2013.01); *B01D 15/265* (2013.01); *C07K 1/20* (2013.01); *C04B 2103/0052* (2013.01)

(58) Field of Classification Search
CPC ........ C07K 16/00; C07K 16/065; C07K 1/20; C07K 1/14; B01D 15/327; B01D 15/26; B01D 15/30; B01D 2311/2626
See application file for complete search history.

(56) References Cited

U.S. PATENT DOCUMENTS

| | | | |
|---|---|---|---|
| 5,095,092 A * | 3/1992 | Badziong | C07K 14/815 530/305 |
| 6,290,853 B1 * | 9/2001 | Allmer | B01D 15/08 210/198.2 |
| 2007/0037734 A1 | 2/2007 | Rossi et al. | |
| 2010/0317827 A1 * | 12/2010 | Dave | B01D 15/325 530/324 |
| 2013/0338344 A1 * | 12/2013 | Ramasubramanyan | C07K 1/165 530/389.2 |

FOREIGN PATENT DOCUMENTS

| | | |
|---|---|---|
| JP | 2000501175 A | 2/2000 |
| JP | 2007533651 A | 11/2007 |
| JP | 2011511062 A | 4/2011 |
| WO | WO2011098526 A1 * | 8/2011 ............... C07K 1/18 |
| WO | 2013162449 A1 | 10/2013 |
| WO | 2015088677 A1 | 6/2015 |
| WO | 2015131978 A1 | 9/2015 |

OTHER PUBLICATIONS

Elgar et al. Simultaneous separation and quantitation of the major bovine whey proteins including proteose peptone and caseinomacropeptide by reversed-phase high-performance liquid chromatography on polystyrene-divinylbenzene. J Chromatogr A. May 12, 2000;878(2):183-96. (Year: 2000).*
Geng et al. Refolding and purification of interferon-gamma in industry by hydrophobic interaction chromatography. J Biotechnol. Sep. 30, 2004;113(1-3):137-49. (Year: 2004).*
AmberchromTM HPR10. Rohm and Haas, 2006 (Year: 2006).*
Bai et al. (2003) Studies on Renaturation with Simultaneous Purification of Recombinant Human Proinsulin from *E.coli* with High Performance Hydrophobic Interaction Chromatography, Journal of Liquid Chromatography & Related Technologies, 26:5, 683-695, DOI: 10.1081/JLC-120018414. (Year: 2003).*
Electrical conductivity of aqueous solutions. CRC Handbook of Chemistry and Physics. p. 5-71. https://sites.chem.colostate.edu/diverdi/all_courses/CRC%20reference%20data/electrical%20conductivity%20of%20aqueous%20solutions.pdf downloaded on Oct. 25, 2018. (Year: 2018).*
GE Healthcare Hydrophobic Interaction and Reversed Phase Chromatography Principles and Methods. Handbook 11-0012-69 AA, 2006. (Year: 2006).*
SourceTM 3ORPC. GE Healthcare, 2009, pp. 1-6. (Year: 2009).*
Hydrophobic Interaction and Reversed Phase Chromatography Principles and Methods. GE Handbook 11-0012-69 AA (2006), pp. 1-168. (Year: 2006).*
International Search Report PCT/EP2015/002306 dated Jan. 3, 2016.
Elgar D F et al: "Simultaneous separation and quantitation of the major bovine whey proteins including proteose peptone and caseinomacropeptide by reversed-phase high-performance liquid chromatography on polystyrene-divinylbenzene", Journal of Chromatography, Elsevier Science Publishers B.V, NL, vol. 878, No. 2, May 1, 2000 (May 1, 2000), pp. 183-196, XP004203726, ISSN: 0021-9673, DOI: 10.1016/S0021-9673(00)00288-0.

(Continued)

*Primary Examiner* — Soren Harward
*Assistant Examiner* — Jia-Hai Lee
(74) *Attorney, Agent, or Firm* — Millen, White, Zelano & Branigan, PC; Ryan Pool

(57) ABSTRACT

The present invention refers to a method for the separation of peptide aggregates and fragments from solutions containing target peptide.

19 Claims, 8 Drawing Sheets

(56) References Cited

OTHER PUBLICATIONS

Sanchayita Ghose et al: "Purification of monoclonal antibodies by hydrophobic interaction chromatography under no-salt conditions", MABS, vol. 5, No. 5, Sep. 1, 2013 (Sep. 1, 2013), pp. 795-800, XP055131308, ISSN: 1942-0862, DOI: 10.4161/mabs.25552.
English translation of Office Action dated Oct. 7, 2019 in corresponding Japan (JP 2017-532058).
Gang et al: "Refolding and purification of interferon-gamma in industry byhydrophobic interaction chromatography", Journal of Biotechnology 113, 2004, 137-149.
Amberchrom(TM) HPR10, ROHM and HAAS, Sep. 2005, [retrieved on Sep. 25, 2019], <https://nshosting.dow.com/docarchive/business/process_chemicals/amberchrom/amberchrom_hpr10/tds/amberchrom_hpr10.pdf>.
Resource RPC / Source 15RPC ST 4.6/100, Source 15RPC, Source 30RPC, GE Healthcare Japan Corporation [retrieved on Sep. 25, 2019], <https://www.gelifesciences.co.jp/catalog/0164.html.
Shalliker et al.; J. Chromatogr. A. (2000) vol.878, issue 2.

\* cited by examiner

TARGET MOLECULE CAPTURE FROM CRUDE SOLUTIONS

The present invention refers to a method for the separation of peptide aggregates and fragments from solutions containing target peptide.

STATE OF THE ART

As recombinantly expressed peptides are used for pharmaceutical applications, they are required in exceptionally high purities [E. P. Kroeff, R. A. Owens, E. L. Campbell, R. D. Johnson, H. I. Marks, Journal of Chromatography, 461 (1989) 45-61].

In response to market pressures for lower cost and higher quantities of biotherapeutics, many manufacturers are considering microbial expression systems (*E. coli*), when possible, as attractive alternatives to mammalian culture. Microbial expression systems feature high productivity and short expression rates, but usually the target molecule is obtained in a denaturated state.

In general, *Escherichia coli* cultures are employed to manufacture the majority of recombinant peptides currently in the market [F. A. O. Marston, Biochem. J. (1986) 240, 1-12]. Production of these therapeutic peptides typically starts in a bioreactor that contains a suspension of cells which produce the therapeutic peptide in high rates, causing its aggregation and formation of inclusion bodies in intracellular fluid. The grown cells are then harvested and disrupted to gain the inclusion bodies containing insoluble target peptide. After target molecule solubilisation and refolding the latter is subjected to a series of processes including clarification, filtration, and purification that removes misfolded peptides, DNA, HCP, aggregates, etc. This series of processes is often referred to as a downstream process (DSP).

Most commonly employed DSP includes one or two bind-elute chromatography purification steps followed by one or two flow-through polishing steps. Typical downstream purification processes employ packed columns filled with porous bead-based chromatography media or membrane-based devices. These unit operations are employed in series and each are targeted towards clearing a particulate impurity in either a flow-through polishing or a bind/elute capture mode. One of the primary objectives of the polishing media is to reduce the concentration of aggregates <1% in reference to target peptide concentration.

As indicated above, usually the target molecule is obtained in a denaturated state. This complicates the purification process, since the target molecule is to be solubilized and refolded prior to final purification. Because of these conditions the process may be very inefficient as the overall yield rates are only in the range of 5 to 10% and as at least 5 time consuming purification steps in a step-by-step mode are needed in the purification process. Moreover, main impurities are aggregated target molecules, which must be removed.

Thus, the peptide refolding process is one of the most challenging production steps [A. Jungbauer, Journal of Biotechnology 128 (2007) 587-596; A. P. J. Middelberg, Trends in Biotechnology Vol. 20 No. 10 Oct. 2002, 437-443], resulting in high target peptide loss due to the formation of insoluble aggregates.

This process is based on a narrow application window (e.g. pH and solvent conductivity dependent) of an ion exchange chromatography mode which is suitable for the capture of the desired target molecule and for the needed primary purification which is followed by additional purification steps using numerous orthogonal technologies (e.g. size-exclusion chromatography, hydrophobic interaction, etc.) in order to reach the biotherapeutical molecule specification. Additionally, subsequential crystallization is implemented to remove the organic solvents used in the final high pressure polishing step.

The manufacturing process for each target molecule is developed individually, corresponding to the physical properties and biotherapeutical molecule specification, increasing the manufacturing costs and time-to-market.

In summary, a typical target peptide purification process is developed individually, corresponding to the physical properties and biotherapeutical molecule specification. Various clarification, filtration, and purification steps are used to purify the target peptide. For example, some technologies are more common, such as ion exchange chromatography and hydrophobic interaction chromatography used for EPO purification [WO 03/045996; WO 00/27869; WO2009/147060]. Other processes include using hydrophobic polystyrene resin (e.g. Source 30RP) as capture step followed directly by the ion exchange step (EP0265222) followed by the hydroxyapatite for the fragment and aggregate separation.

Especially the use of hydroxyapatite is very important for the purification of target molecules from microbial expression systems, since the main process impurity is target molecule aggregates (WO 2005/044856; WO 2010/147686).

Recently, there has been a noticeable trend in the industry to try and reduce the number of purification steps or simplify them maintaining the product quality attributes. Also, use of techniques for obtaining a higher expression titer using bioreactors is a rising trend in the industry. The combination of these two trends has resulted in loading more of the product onto a column, thereby resulting in increased burden of fairly expensive chromatography media as well as lower product purity, both of which are undesirable.

In order to improve the selectivity of the chromatographic purification of desired proteinaceous products like aggregates, various chromatographic materials have been developed in parallel to the alteration of purification methods. Especially specific derivatizations of surfaces of separation materials should lead to a more selective separation of undesired impurities from the desired product. But these special and complex surface derivatizations make the production of these chromatography materials a lot more expensive than commercially available products, so that their use in industrial scale purifications is less attractive.

Other developments in the field of chromatography materials were drawn to separation materials based on organic substrates, because commercially available materials, based on silica materials, are generally affected in a basic milieu and lose stability, particularly during regeneration.

Stationary phases based on organic polymers can be operated over a wide range of pH conditions. Thus, the polymeric resins may be cleaned aggressively under high pH conditions. But current polymeric stationary phases are somewhat compressible at medium to high pressure conditions used in high-performance biomolecule separations.

Conventional macroporous copolymers produced from the suspension polymerization of divinylbenzene (DVB)-containing mixtures in the presence of a non-solvent represent polymers having a wide range of pore size distributions and surface areas. Such polymer beads are for example disclosed in U.S. Pat. No. 4,686,269. These polymer beads are prepared from vinylaromatic monomers, having average particle diameters from 0.5 to 50 μm. But they are not rigid under high pressure conditions commonly used in production scale chromatography columns. Rigidity of polymer beads used in chromatography is essential because it provides together with the porous polymer stationary phase the necessary pressure and flow characteristics during separation.

OBJECT OF THE INVENTION

From the above described prior art results a need for a robust and reliable peptide purification method, which is effectively applicable in a wide range of conditions in a bind and elute mode as well as in flow through mode, and wherein the level of critical impurities, such as aggregates and target peptide fragments is reduced.

The object of the present invention is also to optimize the method and to reduce the number of needed process steps and to accelerate the production process. Another object of the invention is to provide an easily feasible method, and significantly reduced costs for the production and purification of the desired biopharmaceutical molecules.

SUMMARY OF THE INVENTION

Inexpectedly it was found that polystyrene particles can be applied for the capture of the target molecules directly from the filtered cell culture solutions or refold pools in a wide operational window, enabling the separation of fragmented and aggregated forms directly in the elution using non-flammable solutions. The obtained pre-purified target molecule solutions can be directly subjected to ion exchange chromatography for the final purification.

More specifically, the present invention relates to a method for separating peptide aggregates and fragments from solutions containing the target peptide, comprising the steps of
(a) providing the sample containing the target peptide;
(b) contacting the sample with a hydrophobic chromatography material for a suitable period of time and adsorbing the peptides,
(c) recovering the target peptide by use of different solvent compositions and
thereby separating aggregated peptides and peptide fragments from the target peptide.

In particular, the present invention relates to a method as claimed by claims 1 to 17.

Detailed Description of the Invention

The present invention relates to a method for separation of peptide aggregates and fragments from solutions containing the target peptide, wherein a solution containing peptides is contacted with a hydrophobic chromatography material for a suitable period of time whereby the peptides are adsorbed by the hydrophobic chromatography material followed by the selective recovery of the absorbed peptides by use of different solvent compositions. Thereby, the aggregated peptide forms can be partly of fully separated from the target peptide.

In detail, the separation is carried out by use of hydrophobic chromatography material, which is particulate and which is made of cross-linked vinylbenzene, ethylstyrene, poly(ethyl)styrene-divinylbenzene, or of poly(ethyl)styrene-divinylbenzene ethyleneglycol-dimethylacrylate resin. Preferably the resin is composed of cross-linked polymer composed of styrene and divinylbenzene in a ratio 98:2 up to 10:90% by weight. In modified form, the particulate material consists of polystyrene, which is cross-linked with copolymer of divinylbenzene and ethylenglycoldi-methacrylate in a ratio of 98:2 up to 10:90% by weight. Usually, these particulate, hydrophobic chromatographic separation materials have mean particle diameters in the range of 10 µm to 600 µm, preferably in the range of 20 µm to 150 µm, most preferably in the range of 20 µm to 63 µm. Suitable hydrophobic porous polymer beads of this size have preferable pore sizes in the range of 4-500 nm, more preferable in the range of 10-30 nm, most preferred in the range of 13 nm to 25 nm.

The object of the present invention is, in particular, a method for the separation of aggregated peptides from the desired peptide by use of hydrophobic chromatographic separation materials having pore sizes in the range of 4 nm to 500 nm, preferably in the range of 10 nm-30 nm, most preferably in the range of 13 nm to 25 nm for the separation of aggregates, and peptide fragments from solutions containing target peptides. The used hydrophobic chromatographic separation materials of the present invention are preferably made of cross-linked vinylbenzene, crosslinked ethylstyrene, polystyrene/polyethylstyrene-divinylbenzene, or of polystyrene/polyethylstyrene-divinylbenzene ethyleneglycol-dimethylacrylate resin. In an especially preferred embodiment the used hydrophobic, rigid polymer beads described herein, have mean particle diameters in the range of 10 µm to 600 µm, preferably in the range of 20 µm to 150 µm, most preferably in the range of 20 µm to 63 µm, and pore sizes in the range of 4 nm to 500 nm, preferably in the range of 10 nm-30 nm, most preferably in the range of 13 nm to 25 nm.

In order to carry out the separation of aggregated peptides from the desired peptide, an aqueous solution, having a pH value in the range of 2-11, preferably in a range of 3-8 and a conductivity in the range of 1-150 mS/cm, preferably in the range of 2-50 mS/cm, is contacted with a hydrophobic chromatography material. The hydrophobic chromatographic material is exposed to 30-100 mg of target peptide per ml of packed bed, preferably to 50-80 mg of target peptide per ml of packed bed at a flow rate in the range of 150-1000 cm/min, preferably in the range of 300-900 cm/min. After the adsorption of the target peptide the hydrophobic chromatographic material is exposed to an aqueous solution containing organic solvent in direct or gradient manner. Depending on the organic solvent concentration the partial separation between the aggregated and target peptide is achieved. In a particularly preferred embodiment the separation of aggregates is processed after a target molecule refolding step. If required, the purification sequence includes a treatment with an ion exchange resin. Depending on the nature of substances to be separated from the treated fluid either anion or cation exchange resins may be applied in the process step. Preferably a cation exchange resin may be used providing negative charged groups like sulfonic acid or sulfate groups. It has been found that for this purpose an ion exchange material is particularly suitable, which is sold under the trade name Eshmuno® S.

For desorbing the target molecules in a gradient manner the composition of the mobile phase during elution time is changed. For the purpose of the present invention usefully aqueous solvent mixtures are used. Experiments have shown that aqueous mixtures comprising at least one solvent selected from the group dipropylene glycol, diethylen glycol, ethanol, methanol and propanol lead to good separation results. In general, these solvent mixtures comprise further additives for setting the elution. For example, the solvent mixture may be mixed with a certain amount of glycine. In addition, the pH is adjusted by addition of an appropriate buffer for the desired purpose. Depending in what pH range the elution takes place, different buffers are suitable. Thus buffers like tris(hydroxymethyl)-aminomethan (TRIS), acetate or phosphate buffer may be applied. Furthermore, if needed, the solvent mixture may comprise a suitable salt, like sodium chloride.

Detailed information regarding the implementation of corresponding gradient elutions can be found by the expert in literature or in appropriate textbooks, for example in "Preparative Chromatography of Fine Chemicals and Pharmaceutical Agents", Henner Schmidt-Traub, Wiley-VCH Verlag, 2005, p. 152-161.

In various experiments described here it was found that porous hydrophobic interaction materials such as porous poly(di)vinyl aromatic beads are useful for large scale peptide purification. These purification steps can be done in order to reduce the level of one or more impurities present in a sample (e. g., a peptide refolding pools) containing a protein of interest.

For this purpose, the peptide refolding solution is brought into contact with the hydrophobic interaction material, for example into contact with porous hydrophobic polystyrene beads, and incubated for a certain period of time in order to adsorb the target peptide and part or all impurities (e.g. aggregates and fractions). After adsorption, selective desorption of the bound components can be achieved using various ratios of organic solvent. By this procedure, it is possible to selectively reduce unwanted peptide fragments and aggregates from the solution containing the peptide of interest.

Said hydrophobic interaction material is especially suitable to be subjected to post peptide refolding solutions and for selectively reducing the level of aggregated substances by contacting a clarified cell culture solution with the material for a suitable period of time. For carrying out this purification process the hydrophobic interaction material (e. g., polystyrene beads) is incorporated into one or several chromatography column(s) or other devices, such as filter housings and the like. These packed columns are then used for protein purification processes in a bind and elute or flow-through mode, whereby aggregated substances interact stronger with the hydrophobic interaction material and the level of aggregates is reduced. In this case, good purification results are obtained, when the flow velocity is adjusted to be in the range of 150 cm/min-1000 cm/min, and especially between 300-900 cm/min.

Furthermore, in experiments described here, it was found, that good purification results are achievable if the pH of the solution is adjusted to be in a range between pH 2 to 11, and preferably in the range pH 3 to 8.

At the same time, it has proven to be advantageous if the conductivity of the solution is in the range of 1 mS/cm-50 mS/cm, and especially in the range between 2-50 mS/cm.

Further, in experiments described herein, it was found, that good purification results are achievable if organic solvents, such as ethanol, 1-propanol, dipropylenglycol were used to selectively desorb the adsorbed substance from the hydrophobic interaction material.

As demonstrated by the experiments herein, it was found to be especially surprising that high purities of the target peptide can be achieved by the use of hydrophobic interaction materials in form of small porous polymer beads. In some embodiments this material may mainly consists of polystyrene or polyethylstyrene and can be crosslinked by a mixture of hydrophobic and hydrophilic monomers, for example divinylbenzene (DVB) and ethylene glycol dimethacrylate (EGDMA).

The porous polymer beads are typically produced by suspension polymerization. They may be produced in a process, which is for example similar to that disclosed in U.S. Pat. No. 4,382,124 and where porosity is introduced into the copolymer beads by suspension polymerization in the presence of a porogen (also known as "phase extender" or "precipitant"), which is a solvent for the monomer but a nonsolvent for the polymer. Conventional porous polymers, such as those prepared according to U.S. Pat. No. 4,382,124 typically encompass the use of a wide range of porogen types, porogen concentrations relative to the monomer phase, monomer types, crosslinking monomer types, crosslinker levels, polymerization initiators and initiator concentrations. The present invention, however, is based on the unexpected finding that when the ratio of hydrophobic monomers is in a special range, these polymer beads are especially suitable and effective in purification of antibodies from cell culture liquids.

While not wishing to be bound by theory, it is believed that in the case of the present invention the increased capacity for target molecules is primarily achieved when the polymer matrix is altered by increasing the contained shares of hydrophobic molecules in the polymer. This alteration was done considering the balance of the polymer building monomers and of the amount of porogens and of crosslinker levels which altogether influence the parameters of porosity, rigidity and binding capacity of target molecules.

Quite unexpectedly, it was found, that a significantly improved separation of aggregates can be achieved by these selected open porous hydrophobic polymer beads. The porous structure enables rapid diffusion of molecules into and out the polymer matrix, and because of the porosity of the polymer beads a large surface area is available for the interaction with unwanted impurities contained in the cell culture medium. Thus, these materials are very effective in separating a biomolecule in a stationary phase. Most modern, commercial polymeric Reverse Phase Chromatography stationary phases appear to be designed around these criteria, and are used under lower pressure conditions, however, at higher pressure conditions (typically in the range of 10 to 100 bar) these materials are compressible. Fortunately, polymer beads as described here have increased rigidity, and at the same time have a high porosity, thereby providing a high capacity for intraparticle diffusion.

The hydrophobic porous polymer beads used in the present invention are well suited for the removal of aggregates from solutions containing target peptides by contacting the solution with the polymer beads in a liquid chromatography column having a diameter ranging from 1 to 100 cm, preferably in the range of 5 to 50 cm, where the column is operated at pressures up to 100 bar, and preferably at pressure ranging from 0.2 to 80 bar. Typically, preparative scale columns are in the range of 10 to 50 cm and are operated at pressures in the range of 0.2 to 80 bar.

The porous polymer beads according to the present invention are typically spherical copolymer beads having an average particle size diameter up to 200 μm, which is the typical size for polymer beads useful for the separation and purification of biomolecules via high performance reverse phase liquid chromatography (such as in columns ranging from 1 to 100 cm in diameter).

In general, porous separation materials have been found particularly effective when they have average particle size diameters ($d_{50}$) in the range of 10-600 μm, preferably in the range of 20-150 µm, whereas such materials having average particle sizes in the range of 20-63 µm have shown to be particularly effective.

Such hydrophobic separation materials, preferably polystyrene beads, appear to be suitable for the desired separation effect, having pore size in the range of 4-500 nm. Purification experiments have shown that hydrophobic interaction materials, having average pore sizes between 10-30 nm, lead to desirable separation results. These desirable separation results can be further improved when spherical hydrophobic polymer beads are used, which are made from a suitable material and an average pore size in the range between 13-25 nm. Suitable porous polymer beads of the present invention preferably possess surface areas (BET) in the range of 300 to 1000 m$^2$/g (square meters per gram), more preferably in the range of 450 to 850 m$^2$/g, and most preferably in the range of 500 to 800 m$^2$/g.

Suitable monounsaturated vinylaromatic monomers that may be used in the preparation of the porous polymer beads described herein include, but are not limited to styrene, C1-C4-alkyl-substituted styrenes, vinylnaphthalene and vinylanthracene. Preferably the monounsaturated vinylaromatic monomer is selected from one or more of styrene and C1-C4-alkyl-substituted styrenes. Included in the group of suitable C1-C4-alkylsubstituted styrenes are ethylvinylbenzenes, vinyltoluenes, dieethylstyrenes, ethylmethylstyrenes and dimethylstyrenes. It is understood, that any of the various positional isomers of each of the aforementioned vinylaromatic monomers is suitable.

This means, porous polymer beads suitable in the present invention particularly may be prepared using one or more monomer(s) selected from the group consisting of vinylbenzene (styrene), ethylstyrene, divinylbenzene, trivinylbenzene, divinyltoluene, divinylnaphthalene, divinylanthracene, divinylxylene and any structural isomer of these monomers.

Preferably the porous polymers are prepared using copolymers of vinylbenzene (styrene) and divinylbenzene or ethylstyrene and divinylbenzene. In a preferred embodiment of the invention the applied crosslinked porous polymer beads comprise styrene/and divinylbenzene in a weight ratio to one another of from 98:2 to 10:90%.

Optionally aliphatic unsaturated monomers, for example (meth)acrylic acids and alkyl esters of (meth)acrylic acids may also be used in addition to the vinylaromatic monomer for the preparation of said hydrophobic, porous polymer beads described herein. These aliphatic unsaturated monomers may be used as crosslinking agents in the preparation of the desired polymer beads.

Suitable aliphatic crosslinking monomers are selected from the group consisting of ethyleneglycol diacrylate, ethyleneglycol dimethacrylate, trimethylolpropane triacrylate, trimethylolpropane trimethacrylate, dieethyleneglycol divinyl ether and trivinylcyclohexane, and which may be used for the preparation of crosslinked hydrophobic porous polymer beads according to the present invention. The aliphatic monomers can be used alone or in combination with polyvinylaromatic monomers mentioned above as crosslinking monomers.

In both variants, ethyleneglycol dimethacrylate, glycidyl methacrylate, and diethyleneglycol divinyl ether are especially suitable for the preparation of porous beads. Preferably these aliphatic crosslinking monomers are used in combination with polyvinylaromatic crosslinking monomers. Under these conditions, the aliphatic monomers typically are comprised in an amount ranging from 0 to 50% and preferably in an amount ranging from 0 to 30%, based on the total monomer weight used to form the rigid and porous polymer beads.

In the inventive use of porous polymer particles described herein superior separation results are achieved using porous polymer beads consisting of polystyrene, which is crosslinked with a copolymer of divinylbenzene or a derivative thereof and a monomer selected from the group consisting of ethyleneglycol dimethacrylate, and diethyleneglycol divinyl ether and wherein the ratio of polystyrene and crosslinking copolymer is in a range of 98:2 up to 10:90% by weight. In a preferred embodiment porous particles consisting of poly(ethyl)styrene are used, which are crosslinked with copolymer of divinylbentzene and ethyleneglycol methacrylate in a ratio of 98:2 up to 14:86% by weight. In this connection, it has been found that for the separation of aggregated substances from solutions containing target peptide, porous beads are better suited, in which (di)vinylaromatic monomers are contained in an amount of more than 50% by weight. Thus porous beads, consisting of polymer of monovinylaromatics, which is crosslinked with copolymer of divinylbenzene and ethyleneglycol methacrylate in a ratio of about 10:90 to 98:2% by weight are preferred. More preferred are such porous beads wherein the ratio is about 14:86 by weight.

Preferred hydrophobic porous polymers are selected from one or more of vinylbenzene (styrene) copolymer, ethylvinylbenzene (ethylstyrene) copolymer, divinylbenzene copolymer, crosslinked polystyrene-divinylbenzene copolymer, crosslinked polystyrene ethyleneglycol-dimethacrylate, crosslinked polydivinylbenzene ethyleneglycol-dimethacrylate. Most preferred are crosslinked poly(ethyl)styrene-divinylbenzene copolymer and poly(ethyl)styrene crosslinked with copolymer of divinylbenzene and ethyleneglycol-dimethacrylate.

Porogens useful for preparing the porous polymers include hydrophobic porogens, such as ($C_7$-$C_{10}$)aromatic hydrocarbons, and ($C_6$-$C_{12}$) saturated hydrocarbons and hydrophilic porogens, such as ($C_4$-$C_{10}$) alkanols and polyalkylene glycols. Thus suitable porogens can, for example, be selected from the group consisting of toluene, ethylbenzene, ortho-xylene, meta-xylene, para-xylene. It is understood that, any of the various positional isomers of any of the aforementioned hydrocarbons is suitable. Preferably, the aromatic hydrocarbon is toluene or xylene or a mixture of xylenes or a mixture of toluene and xylene. Furthermore as indicated above, saturated hydrocarbons can also be used as porogens. Suitable examples include, but are not limited to are for example hexane, heptanes or isooctane. The preferred saturated hydrocarbon in this case of the present invention is isooctane. Suitable alkanols include, but are not limited to isobutyl alcohol, tert-amyl alcohol, n-amyl alcohol, isoamyl alcohol, methyl isobutyl carbinol, (4-methyl-2-pentanol), hexanols and octanols. Preferably a porogen mixture comprises a hydrophilic porogen selected from one or more ($C_5$-$C_8$)alkanol and a hydrophobic porogen selected from one or more ($C_7$-$C_{18}$)aromatic hydrocarbon.

Typically the porogen is added to the polymerization suspension in excess, usually in a total amount of 100 to 170%, preferably from 115-150 and more preferably from 120 to 140%, based on weight of the monomers. In addition, the porogens used to prepare the polymers according to the present invention are mixed with a solvent system, which comprises at least a hydrophobic solvent and optionally a less hydrophobic solvent ("hydrophilic" solvent) and which both support the building of porous beads. It is self-explanatory that the less hydrophobic (or "hydrophilic" as stated above) solvent has at least some limited water solubility, for example, ranging from 0.5 to 5% whereas the hydrophobic solvent shows a water solubility of 10 to 100 ppm or less.

Generally, the ratio of porogen with low hydrophobicity (i. e., "hydrophilic porogen") to the hydrophobic porogen is in the range of 0.7:1 up to 3:1, preferably in the range of 0.8:1 up to 2.5:1, most preferably from 0.9:1 to 2.4:1.

Polymerization initiators useful in preparing polymers suitable in the present invention are well known to one of ordinary skill in the art and include monomer soluble initiators like peroxides, hydroperoxides, and related initiators. These initiators are commercially available. Also useful are azo initiators such as azodiisobutyronitrile, azodiisobutyramide and the like. Depending on the nature of the initiator the use levels are in ranges of 0.5 to 10% based on the total weight of the comprising vinyl monomers.

Furthermore, dispersants or suspending agents useful for preparing the porous polymer beads may be customary surfactants, which are ionic and may contain hydrophobic alkyl chains containing 1 to 24 carbon atoms. Another commercially available group of dispersants which is suitable in the suspension polymerization are nonionic surfactants, which are based on epoxidized hydroxyalkylcellulose derivatives. Typically these additives are used at levels of about 0.01 up to 4% based on the total weight of the aqueous phase.

If suitable, other dispersants may be used and can be applied together with those surfactants and dispersants. For example, polymeric dispersants including celluloses, polyvinyl pyrrolidones, polyvinyl alcohols, starches and the like may be used in mixtures with other surfactants or dispersants used herein. But most preferred is the addition of ionic surfactants, which can be easily removed from the prepared polymer beads by rinsing with water.

For the preparation of the porous hydrophobic polymer beads disclosed herein, a continuous aqueous phase solution containing suspension aids is prepared and then this solution is mixed with a monomer mixture containing the polyvinylaromatic monomer, free-radical initiator and for example 1 to 1.7 parts of (mixed) porogen (hydrophobic and hydrophilic porogen) per one part monomer mixture. The monomer/porogen combinations then polymerized at elevated temperature (typically at 40 to 100° C., for example for 1 to about 15 hours) and the porogens are subsequently removed from the resulting polymer beads, for example by distillation or solvent washing. The resulting porous polymer beads are then isolated by conventional means, like dewatering and drying.

Optionally the preparation of the polymer beads may include a treatment to cleanse the polymer surface of residues of dispersants and suspending agents used during the polymerization. This treatment may include an enzyme treatment as disclosed in the patent literature (JP 61-141704 or JP 57-98504 or EP 1 179 732 B1)

Prepared polymer beads are especially suitable in packed columns, because of their porosity and mechanical strength. Advantageously, these porous and rigid polymer beads are useful for the separation of aggregated substances from solutions containing target peptide by contacting the solution with these polymer beads in liquid chromatography columns even at elevated pressures. These beads are especially suitable for high performance separations and purifications of biomolecules at high throughput rates without pressure buildup because of prolonged use.

Porous polymer beads as used in the present invention are characterized by selected porosities and pore size distributions, which may be determined by inverse size-exclusion chromatography (iSEC). The polymer beads suitable in the present invention typically have a porosity ε in the range of 0.4 to 1.0 and preferably in the range of 0.45 to 0.75. These beads possess surface area ranging from 300 to 100 $m^2/g$ [BET], more preferably from 450 to 850 $m^2/g$, and most preferably in the very narrow range of 500 to 800 $m^2/g$.

The polymer beads as disclosed here are unexpectedly well suited for the separation of aggregated substances from solutions containing target peptides. Because of their chemical nature and their nano porous structure these materials are especially suitable for hydrophobic interaction with low molecular weight proteins and peptides and can be incorporated into chromatography column based purification processes in a bind and elute or flow-through mode. Advantageously the applied polystyrene beads need not to be derivatized and, therefore are much more cost effective than commonly used chromatography gels in this purification step. The separation materials described herein are fairly inexpensive and can be regenerated, thereby reducing the overall costs of peptide purification platform and beyond.

Additionally, the application of hydrophobic material is not limited to the given examples, since it is based on size exclusion mechanisms and hydrophobic adsorption of low molecular weight substances, especially compounds of molecular mass <70 kDa.

Furthermore, the present invention provides a chromatography based antibody purification step, wherein the chromatography material described herein can be regenerated and is applicable in wide operation window (e. g. pH 3-11; conductivity 1 mS/cm-50 mS/cm, operational velocity 150 cm/min-1000 cm/min). In particular, the resistance of the porous polymer beads at low and high pH values is of great advantage here because a satisfactory regeneration is possible and these materials have a considerably longer life span.

As already indicated above, the adsorption of low molecular weight substances, especially compounds of molecular mass <70 kDa, from peptide solutions using the hydrophobic porous polymer beads described herein may be performed both at industrial and as well as micro-scale, as the selected separation materials are stable against pressure and are not prone to deformation at high pressures. The user is free in the manner of carrying out the chromatographic purification. It is self-explanatory that depending on the nature of the applied solution and of the low molecular weight proteins and peptides, one or the other composition of the porous polymer particles may be advantageous for the purification step. Here the expert has the choice between porous polymers made from pure (vinyl)alkyl aromatics or those that are crosslinked by suitable acrylates. In this case, the most suitable polymers beads can be readily identified by one of ordinary skill in the art.

The present description enables one of ordinary skill in the art to practice the present invention comprehensively. Even without further comments, it is therefore assumed that a person of ordinary skill in the art will be able to utilise the above description in the broadest scope.

If anything is unclear, it is understood that the publications and patent literature cited should be consulted. Accordingly, these documents are regarded as part of the disclosure content of the present description.

For better understanding and in order to illustrate the invention, examples are described below which are within the scope of protection of the present invention. These examples also serve to illustrate possible variants.

Furthermore, it goes without saying to one of ordinary skill in the art that, both in the examples given and also in the remainder of the description, the component amounts present in the compositions always only add up to 100% by weight or mol %, based on the composition as a whole, and cannot exceed this percentage, even if higher values could arise from the percent ranges indicated. Unless indicated otherwise, % data are therefore % by weight or mol %, with the exception of ratios, which are shown in volume data.

As used throughout the specification, the following terms shall have the following meanings, unless the context clearly indicates otherwise:

The term "alkyl(meth)acrylate" refers to either corresponding acrylate or methacrylate ester; similarly, the term "(meth)acrylic" refers to either acrylic or methacrylic acid and the corresponding derivatives, such as esters or amides. As indicated above, all percentages referred to will be expressed in weight percent (%), based on total weight of polymer or composition (solution) involved, unless specified otherwise. The term "copolymer" refers to polymer compositions containing units of two or more different monomers, including positional isomers.

The following abbreviations are used herein:
g=grams,
ppm=parts per million by weight/volume,
m=meter,
cm=centimeter,
mm=millimeter,
μm=micrometer (micron)=$10^{-6}$ m,
nm=nanometer=$10^{-9}$ m,
ml=milliliter, L=Liter. Unless otherwise specified, ranges listed are to be read as inclusive and combinable.

The temperatures given in the examples and the description as well as in the claims are always degrees centigrade (° C.).

Methods:

Particle Characteristics:

Characterization of particles is known in the art and is described by: I. C. Edmundson. Particle-size analysis, H. S. Bean, A. H. Beckett and J. E. Caries (eds) in: Advances in Pharmaceutical Sciences vol 2, Academic Press, London 1967, 95-174.

The particle size distribution and the average diameter may be measured by laser diffractometry using Mastersizer 2000E (Malvern Instruments Ltd., UK) or by a laser light blocking technique (Accusizer™, model 770, Particle Sizing Systems, Santa Barbara, Calif., USA).

The shape and surface characteristics (porosity) of the microspheres may be established by scanning electron microscopy (SEM) analysis.

The pore size is determined by methods which are known in the art. Macropores may be determined using mercury porosimetry. In this case experiments for analyzing pore sizes are done following the protocol of the used mercury porosimetry analyzer (e. g. AutoPore IV 9500, Micromeritics, USA). It is also possible to estimate the pore dimensions from scanning electron micrographs (SEM) where the diameter and surface features of the polymer microspheres are observed after drying by scanning electron microscope (SEM) (JSM-6700F. JEOL, Japan). Microspheres are resuspended in distilled water and the dispersion is dropped on a piece of aluminum foil and dried at ambient atmosphere. The sample is placed on a metal stub with double-sided conductive adhesive tape and is coated with a thin gold film under reduced pressure below 5 Pa with a JFC-1600 fine coater (JEOL, Japan).

The pore size of mesopores and their specific surface area can also determined using nitrogen adsorption/desorption measurements (BET-method), which are performed by following standard protocols. This latter method may also be used for determining the BET surface area.

BRIEF DESCRIPTION OF DRAWINGS

FIG. 4: Non-reducing SDS-PAGE of dynamic capture raw insulin on P00446 (Column 1.1 ml diameter 10 mm). using ÄKTA FPLC system. 10 CV Equillibration with 25 mM Tris, 100 mM Arginine, pH 7. 30 ml of 1 mg/ml raw insulin were loaded with 1 ml/min flowrate. Elution in 20 CV from 0% till 100% 60 Vol. % DPG. Lanes: M—molecular weight marker; S—start material; FT—flow through.

EXAMPLES

Figure 1:
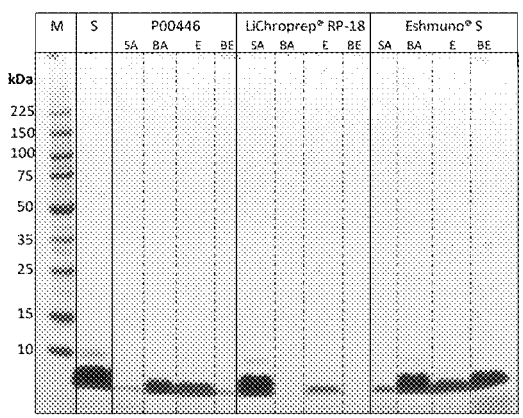
FIG. 1: Non-reducing SDS-PAGE of static capture insulin on P00446, LiChroprep® RP-18 and Eshmuno® S. 1 ml of 5 mg/ml insulin @ 50 mM Acetate pH 4 was added to 100 μl equilibrated particles. Adsorption for 30 minutes @ 25° C. Elution for 30 minutes @25° C. with 500 μl 50 mM Acetate, 40 Vol % DPG, pH 4 respectively 50 mM phosphate, 500 mM NaCl, pH 8 for Eshmuno® S. Indicated lanes: M—molecular weight marker; S—start material, SA—supernatant after adsorption, BA—beads after adsorption.

Base Beads:
Synthesis of Polystyrene Based Material (Such as P353, P374 and P375)

25.6 g Polyvinylalcohol and 0.38 g SDS are dissolved in 614.2 g water to form the water phase for the following suspension polymerization. The organic phase is formed by a homogenous solution of 19.94 g ethylvinylbenzene, 75 g divinylbenzene, 41.57 g ethylene glycol dimethacrylate, 90.24 g toluene, 90.24 g 2-ethyl-1-hexanole and 0.96 g AIBN. The organic phase is added to the water phase in a reactor vessel and the two phases are emulsified at 25° C. with a stirrer at 480 rpm to achieve the anticipated particle size distribution. After 60 min 640 g water are added and the reaction mixture is heated up to 72° C. For two hours the temperature is kept at 72° C. and then increased to 82° C. The mixture is polymerized at 82° C. for additional two hours. Following polymerization the suspension is filtered on a filter funnel and the particles are washed with 1.5 liter water of 60° C., followed by 5 liter methanol at 60° C., 5 liter of toluene and 2 liter of methanol at 40° C. The final product is dried in a vacuum oven for 24 hours at 50° C. and 50 mbar. The yield regarding dry mass is quantitative. Depending from the anticipated particle size distribution the final product is classified by sieving according to procedures which are state of the art.

Example 1

In this experiment, different materials are evaluated for their ability to adsorb recombinant peptide-insulin. For the following example Polystyrene (PS) particles P00446 are used for capture of pure insulin (A11382IM, life technologies) in comparison to the common used LiChroprep® RP-18 (113900, Merck Millipore) beads and one cation exchange material (e.g. Eshmuno® S, 120078, Merck Millipore). 100 µl particles are washed with 1 ml of 50 mM Acetate pH 4. Afterwards 1 ml of a 5 mg/ml insulin solution in 50 mM Acetate pH 4 was adsorbed for 30 minutes at 25° C. After centrifugation the supernatant is removed (5 µl were mixed with 5 µl gel loading buffer, NP0007, life technologies). Particles are washed with 1 ml 50 mM Acetate pH 4 and split in 2 tubes. After centrifugation the supernatant is discarded. For beads after adsorption one part of the particles are resuspended in 500 µl gel loading buffer. The other part is eluted with 500 µl of 50 mM Acetate, 40 Vol % DPG, pH 4 respectively 50 mM phosphate, 500 mM NaCl, pH 8 for Eshmuno® S for 30 minutes at 25° C. After centrifugation the supernatant is removed (5 µl were mixed with 5 µl gel loading buffer). Particles are washed with 500 µl 50 mM Acetate pH 4. After centrifugation the supernatant is discarded. For beads after elution the particles are resuspended in 500 µl gel loading buffer. After heating all samples for 10 minutes at 99° C. 10 µl of supernatant/eluate respectively 5 µl of bead-samples are loaded on 4-12% NuPAGE® Novex® Bis-Tris Gel (NP0336, life technologies). Gel is run for 25 minutes at 200 V constant. After washing with pure water it is stained with SimplyBlue™ SafeStain (LC6065, life technologies) and destained with pure water.

As shown in FIG. 1 the polystyrene beads P00446 adsorb insulin nearly complete which corresponds to a static binding capacity of 50 mg protein per ml particle-suspension. 40 Vol % Dipropylene glycol is a useful desorption solution. The new technology of PS particles is comparable to the common used cation exchange process. In comparison LiChroprep® RP-18 (as an alternative reverse phase material) does not adsorb insulin under the given conditions.

Example 2

Figure 2:
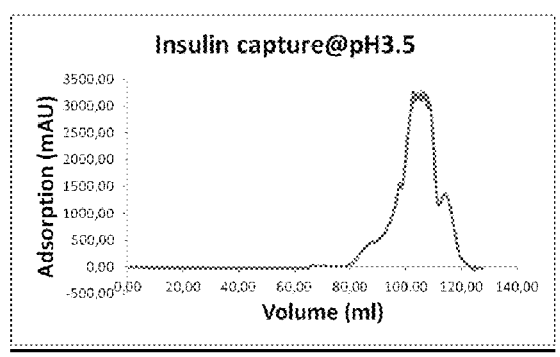
FIG. 2: Elution peak of the captured crude insulin from P00446 polystyrene particles

In this experiment, different materials are evaluated for their ability to adsorb crude insulin A. For the following example Polystyrene (PS) particles P00446 are packed in a 10 mm diameter 12 mm long column using 20% ethanol 150 mM NaCl solution. The packed column is equilibrated using 50 mM Glycine/50 mM Acetic acid buffer pH 3.5 for at least 20 column volumes at 1 ml/min. The crude insulin solution A is adjusted to pH 3.5 (insulin concentration~1.7 g/L). 60 ml of obtained solution is directly loaded on the equilibrated column at 1 ml/min and the flow through fraction collected in a separate flask. After loading, column is washed with 10CV using equilibration solution. The elution of the captured crude insulin is performed using a gradient elution from 0-100% of 50% ethanol in 50 mM Glycine/50 mM Acetic acid buffer pH 3.5 in 30 CV at 1 ml/min (FIG. 2). The fractions are collected and subjected to non-reducing SDS-PAGE analysis (FIG. 3).

Figure 3:
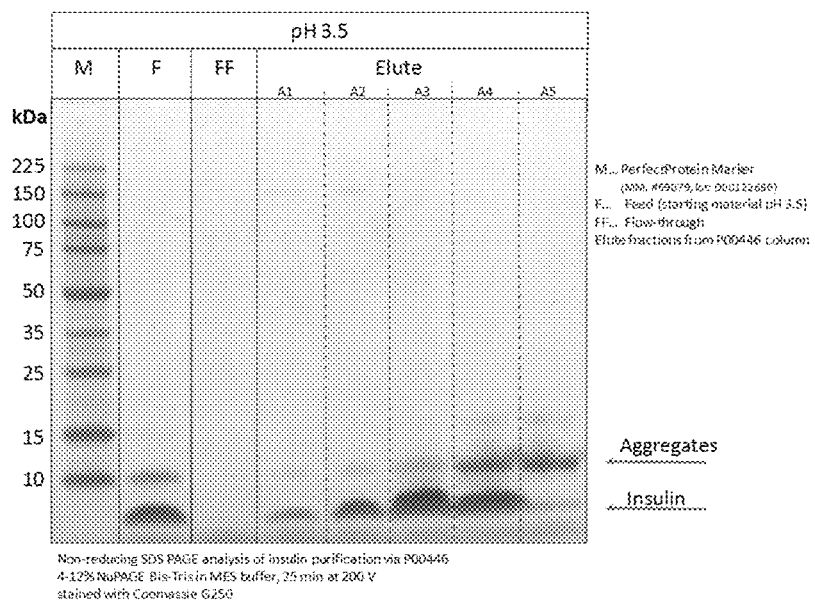
FIG. 3: Non-reducing SDS-PAGE of dynamic crude insulin capture on P00446. Indicated lanes: M—Perfect Protein Marker; F—feed (starting material at pH 3.5), FF—flow through, A1-A5—elute fractions

As shown in FIG. 3 the polystyrene beads P00446 adsorb insulin nearly complete which correspond to a binding capacity of >80 mg protein per ml packed bed. 50 Vol % ethanol is a useful desorption solution (e.g. recovery 101.33%), enabling to use polystyrene particles for aggregate and target molecule separation, that is not noticed using ion exchangers for the crude insulin capture (data not shown).

Example 3

In this experiment, particulate material, consisting of poly(ethy)styrene (m) crosslinked with divinylbenzene copolymers (PS-DVB), is evaluated for its ability to adsorb crude insulin B. For the following example Polystyrene (PS)

particles P00446 are packed in a 10 mm diameter 12 mm long column using 20% ethanol 150 mM NaCl solution. The packed column is equilibrated using 50 mM TRIS, 100 mM Arginine buffer pH 7.0 for at least 20 column volumes at 1 ml/min. The crude insulin solution B originating from E. coli expression system is adjusted to pH 3.5 and 30 ml of obtained solution is directly loaded on the equilibrated column at 1 ml/min and the flow through fraction collected in a separate flask. After loading, column is washed with 10CV using equilibration solution. The elution of the captured crude insulin is performed using a gradient elution from 0-100% of 60% dipropylenglycol in 50 mM Glycine/50 mM Acetic acid buffer pH 3.5 in 20 CV at 1 ml/min. The fractions are collected and subjected to non-reducing SDS-PAGE analysis (FIG. 4).

Figure 4:
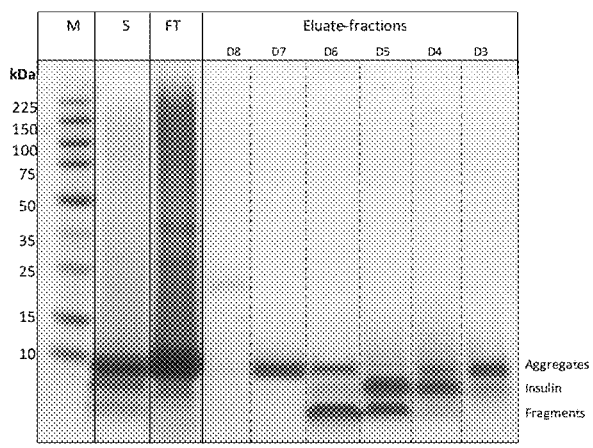

As shown in FIG. 4 the polystyrene beads P00446 adsorb insulin (5% purity) from the crude solution and dipropylenglycol solution can be applied to separate insulin fragments from aggregates and target achieving >40% purity.

Example 4

In this experiment, particulate materials consisting of poly(ethyl)styrene (m), crosslinked with divinylbenzene copolymers (PS-DVB) are evaluated for their ability to adsorb crude protein pSCP194. For the following example Polystyrene (PS) particles P00446 are packed in a 10 mm diameter 12 mm long column using 20% ethanol 150 mM NaCl solution. The packed column is equilibrated using 50 mM TRIS, 100 mM Arginine buffer pH 7.0 for at least 20 column volumes at 1 ml/min. The crude E. coli lysate containing protein pSCP194 is adjusted to pH 7.0 and 20 ml of obtained solution is directly loaded on the equilibrated column at 1 ml/min and the flow through fraction collected in a separate flask. After loading, column is washed with 10CV using equilibration solution. The elution of the captured crude insulin is performed using a gradient elution from 0-100% of 60% dipropylenglycol in 50 mM Glycine/50 mM Acetic acid buffer pH 3.5 in 20 CV at 1 ml/min. The fractions are collected and subjected to non-reducing SDS-PAGE analysis (FIG. 5).

Figure 5:
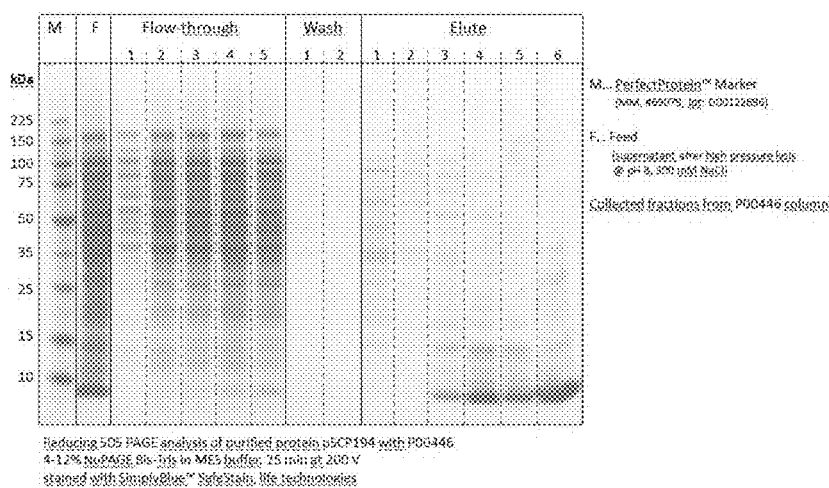
FIG. 5: Non-reducing SDS-PAGE of dynamic crude pSCP194 capture on P00446 (Column 1.1 ml diameter 10 mm). Lanes: M—PerfectProtein™ molecular weight marker; F—feed (supernatant after high pressure lysis of cells @ pH 8.0, 300 mM NaCl); collected fractions from P00446 column: flow through, wash, elute).

As shown in FIG. 5 the polystyrene beads P00446 adsorb pSCP194 protein from the crude e. coli lysate solution and dipropylenglycol solution can be applied to elute the captured target achieving >80% purity.

Example 5

In this experiment, particulate material consisting of poly (ethyl)styrene (m), crosslinked with divinylbenzene copolymers (PS-DVB) and material consisting of ethylene glycol dimethylacrylate (PS-DVB-EGDMA) copolymers in various ratios is evaluated for its ability adsorb insulin in presence of urea.
For the following example Polystyrene (PS) particles P00446 are packed in a 10 mm diameter 12 mm long column using 20% ethanol 150 mM NaCl solution. The packed column is equilibrated using 50 mM Glycine/50 mM acetic acid buffer pH 3.5 for at least 20 column volumes at 1 ml/min. The crude insulin solution containing aggregated insulin after incubation in 8M urea solution is diluted to 2M urea concentration using pure water adjusted to pH 3.5. 50 ml of obtained solution is directly loaded on the equilibrated column at 1 ml/min and the flow through fraction collected in a separate flask. After loading, the column is washed with 10CV using equilibration solution. The elution of the captured crude insulin is performed using a gradient elution from 0-100% of 60% dipropylenglycol in 50 mM Glycine/50 mM Acetic acid buffer pH 3.5 in 20 CV at 1 ml/min. The fractions were collected and subjected to non-reducing SDS-PAGE analysis (FIG. 6).

Figure 6:
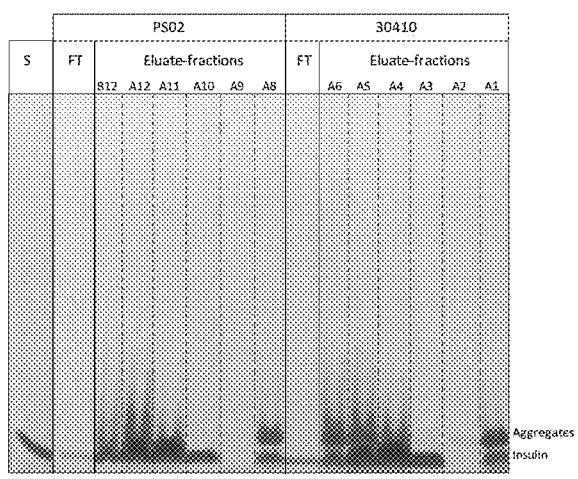
FIG. 6: Non-reducing SDS-PAGE of dynamic crude insulin capture on P00446 and PS02 (Column 1.1 ml diameter 10 mm). Lanes: S—start material, FT—flow through fraction, PS02 B12-A8 elute fractions, 30410 A6-A1 elute fractions.

As shown in FIG. 6 the polystyrene beads P00446 and PS02 adsorb insulin from the crude 2M urea containing solution and dipropylenglycol solution can be applied to elute the captured target achieving >90% purity (fractions A3-A4 and A11-A12).

Example 6

Figure 7:
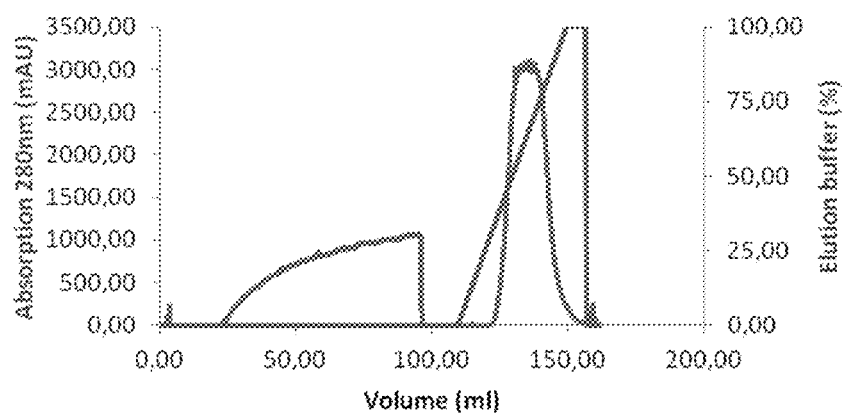
FIG. 7: Chromatogram of Insulin/aggregates purification with PP00446 at pH 3.5 using a linear gradient and Dipropylene glycol in elution buffer.

In this experiment, particulate material consisting of poly (ethyl)styrene (m), crosslinked with divinylbenzene copolymers (PS-DVB) and ethylene glycol dimethylacrylate (PS-DVB-EGDMA) copolymers in various ratios, is evaluated for its ability to purifying Insulin from its aggregates at pH 3.5 using a linear elution gradient and Dipropylene glycol organic solvent in aqueous buffer. For the following example 1 ml Polystyrene (PS) particles PP00446 are packed in a 10 mm diameter 6.2 long column using grinding beads for lengthening the column. For column packing 20% Ethanol 150 mM NaCl is prepared. The packed column is equilibrated using 50 mM Glycine/50 mM Acetic acid pH 3.5 (equilibration buffer) for 20 column volumes at 1 ml/min. The Insulin/aggregates solution is adjusted to pH 3.5 by adding acetic acid (insulin concentration: ~1.5 mg/ml). 92 ml of prepared solution is loaded on the equilibrated column at 1 ml/min while the flow through is collected in a flask. After accomplished loading the column is rinsed with equilibration buffer for 15 column volumes at 1 ml/min to wash out unbound Insulin molecules. The flow through during the wash out step is collected in a second flask. Subsequently the elution is initialized using a linear gradient from 0-100% of 50% Dipropylene glycol in 50 mM Glycine/50 mM Acetic acid (elution buffer) in 40 column volumes at 1 ml/min. The eluates are fractionated in 10 ml per fraction. FIG. 7 depicts the chromatogram recorded during the Insulin/aggregates purification. The collected fractions are subjected to non-reducing SDS-PAGE analysis (FIG. 8).

Figure 8:
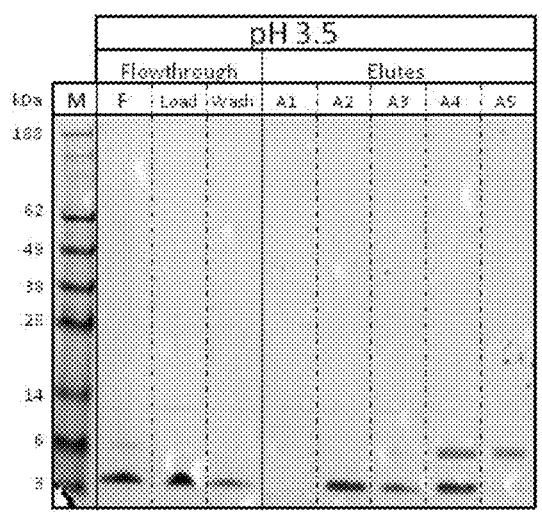
FIG. 8: Non-reducing SDS-PAGE analysis of all fractions during the Insulin/aggregates purification with PP00446 at pH 3.5 using a linear gradient and Dipropylene glycol in elution buffer. Lanes: M—SeeBlue®Plus2 Prestained Standard, F—Feed Insulin starting material@pH 3.5, Load—flowthrough collection during loading, Wash—flow through collection during wash step, elutes—elute fraction A1-A5 from P00446 column. Elution conditions: 50% DPG in 50 mM Glycine, 50 mM Acetic acid pH 3.5 gradient.

As shown in FIG. 8 PP00446 resin is overloaded by Insulin/aggregates solution. The measured dynamic binding capacity of PP00446 reached >80 mg protein per ml packed bed. It becomes apparent that 50 Vol % Diproylene glycol is not only a suitable desorption solution (e.g. recovery: 115%), but also enable the separation of Insulin from its aggregates during linear gradient elution.

Example 7

Figure 9:
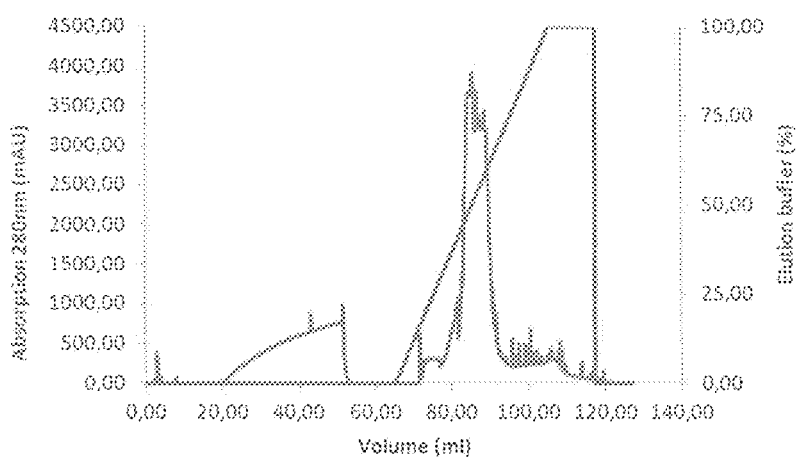
FIG. 9: Chromatogram of Insulin/aggregates purification with PP00446 at pH 3.5 using a linear gradient and Ethanol in elution buffer.

In this experiment, particulate materials consisting of poly(ethyl)styrene (m) crosslinked with divinylbenzene copolymers (PS-DVB) and ethylene glycol dimethylacrylate (PS-DVB-EGDMA) copolymers in various ratios is evaluated for its ability to purifying Insulin from its aggregates at pH 3.5 using a linear elution gradient and ethanol. For the following example 1 ml Polystyrene (PS) particles PP00446 are packed in a 10 mm diameter 6.2 long column using grinding beads for lengthening the column. For column packing 20% Ethanol 150 mM NaCl is prepared. The packed column is equilibrated using 50 mM Glycine/50 mM Acetic acid pH 3.5 (equilibration buffer) for 20 column volumes at 1 ml/min. The Insulin/aggregates solution is adjusted to pH 3.5 by adding acetic acid (insulin concentration: ~2.0 mg/ml). 50 ml of prepared solution is loaded on the equilibrated column at 1 ml/min while the flow through is collected in a flask. After accomplished loading the column is rinsed with equilibration buffer for 15 column volumes at 1 ml/min to wash out unbound Insulin molecules. The flow through during the wash out step is collected in a second flask. Subsequently the elution was initialized using a linear gradient from 0-100% of 50% Ethanol in 50 mM Glycine/50 mM Acetic acid (elution buffer) in 40 column volumes at 1 ml/min. The elutes were fractionated in 10 ml per fraction. FIG. 3 depicts the chromatogram recorded during the Insulin/aggregates purification. The collected fractions are subjected to non-reducing SDS-PAGE analysis (FIG. 9).

Figure 10:
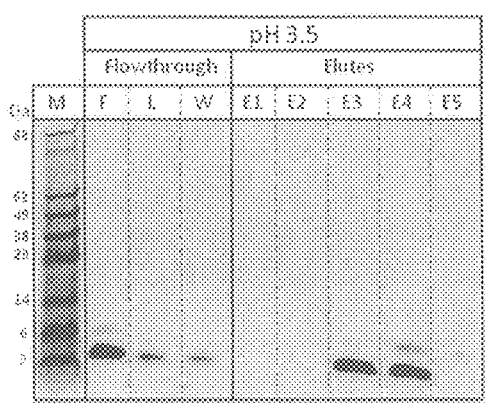
FIG. 10: Non-reducing SDS-PAGE analysis of all fractions during the Insulin/aggregates purification with PP00446 at pH 3.5 using a linear gradient and Ethanol in elution buffer. Lanes: M—SeeBlue®Plus2 Prestained Standard, F—Feed Insulin starting material@pH 3.5, L—flowthrough collection during loading, W—flow through collection during wash step, elutes—elute fraction E1-E5 from P00446 column. Elution conditions: 50% DPG in 50 mM Glycine, 50 mM Acetic acid pH 3.5 gradient.

As shown in FIG. 10 PP00446 resin is overloaded by Insulin/aggregates solution. The measured dynamic binding capacity (DBC) of PP00446 reached >60 mg protein per ml packed bed. The results expose that 50 Vol % Ethanol can be used as desorption solution (recovery: 96%). In contrast to the elution under comparable conditions with Dipropylene glycol, the purification from this example results in lower DBC as well as in deteriorated recovery.

Example 8

In this experiment, particulate materials consisting of poly(ethyl)styrene (m) crosslinked with divinylbenzene (PS-DVB) and ethylene glycol dimethylacrylate (PS-DVB-EGDMA) copolymers in various ratios is evaluated for its ability to separate insulin from its aggregates at pH 8.0 using a linear elution gradient and dipropylen glycol.

Figure 11:
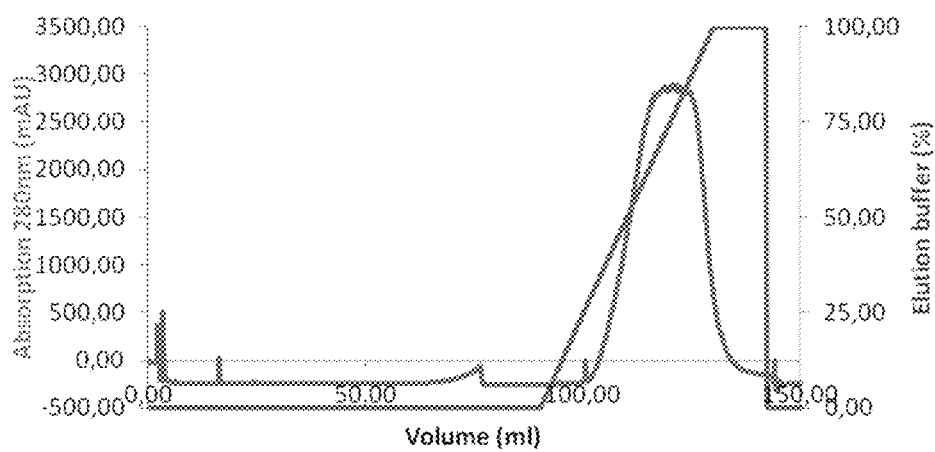
FIG. 11: Chromatogram of Insulin/aggregates purification with PP00446 at pH 8.0 using a linear gradient and Dipropylene glycol in elution buffer.

For the following example 1 ml Polystyrene (PS) particles PP00446 are packed in a 10 mm diameter 6.2 long column using grinding beads for lengthening the column. For column packing 20% Ethanol 150 mM NaCl is prepared. The packed column is equilibrated using 50 mM TRIS pH 8.0 (equilibration buffer) for 20 column volumes at 1 ml/min. The Insulin/aggregates solution is adjusted to pH 8.0 by adding 1M TRIS. Furthermore the conductivity of the Insulin/aggregates solution is set to ~20 mS/cm by 1M NaCl solution (insulin concentration: ~0.6 mg/ml). 75 ml of prepared solution was loaded on the equilibrated column at 1 ml/min while the flow through is collected in a flask. After accomplished loading the column is rinsed with equilibration buffer for 15 column volumes at 1 ml/min to wash out unbound Insulin molecules. The flow through during the wash out step is collected in a second flask. Subsequently the elution is initialized using a linear gradient from 0-100% of 50% Dipropylene glycol in 50 mM TRIS pH 8.0 (elution buffer) in 40 column volumes at 1 ml/min. The elutes are fractionated in 10 ml per fraction. FIG. 5 depicts the chromatogram recorded during the Insulin/aggregates purification. The collected fractions are subjected to non-reducing SDS-PAGE analysis (FIG. 11).

Figure 12:
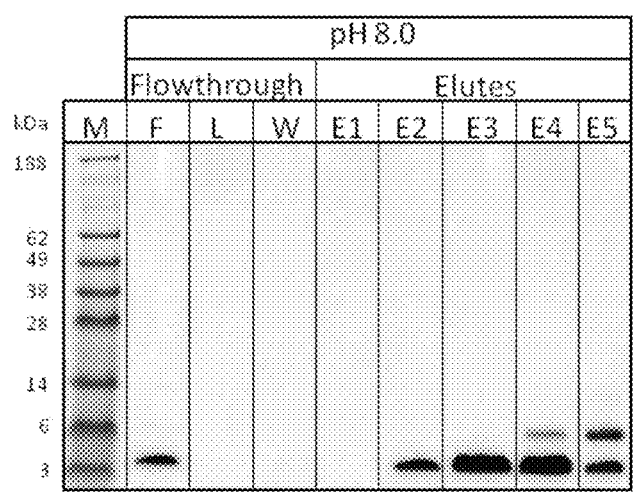
FIG. 12: Non-reducing SDS-PAGE analysis of all fractions during the Insulin/aggregates purification with PP00446 at pH 8.0 using a linear gradient and Dipropylene glycol in elution buffer. Lanes: M—SeeBlue®Plus2 Prestained Standard, F—Feed Insulin starting material@pH 8.0, L—flowthrough collection during loading, W—flow through collection during wash step, elutes—elute fraction E1-E5 from P00446 column. Elution conditions: 50% DPG in 50 mM TRIS pH 8.0 gradient.

As shown in FIG. 12 PP00446 resin adsorbs insulin and its aggregates nearly completely and reaches a dynamic binding capacity of >70 mg protein per ml packed bed. Moreover by the application of a linear gradient the elution results in purifying Insulin from aggregates (E2, E3), whereas most aggregates are desorbed at an elution buffer concentration >80%.

Example 9

In this experiment, particulate materials consisting of poly(ethyl)styrene (m) crosslinked with divinylbenzene (PS-DVB) and ethylene glycol dimethylacrylate (PS-DVB-EGDMA) copolymers in various ratios is evaluated for its ability to separate insulin from its aggregates at pH 8.0 using a step elution and dipropylen glycol.

Figure 13:
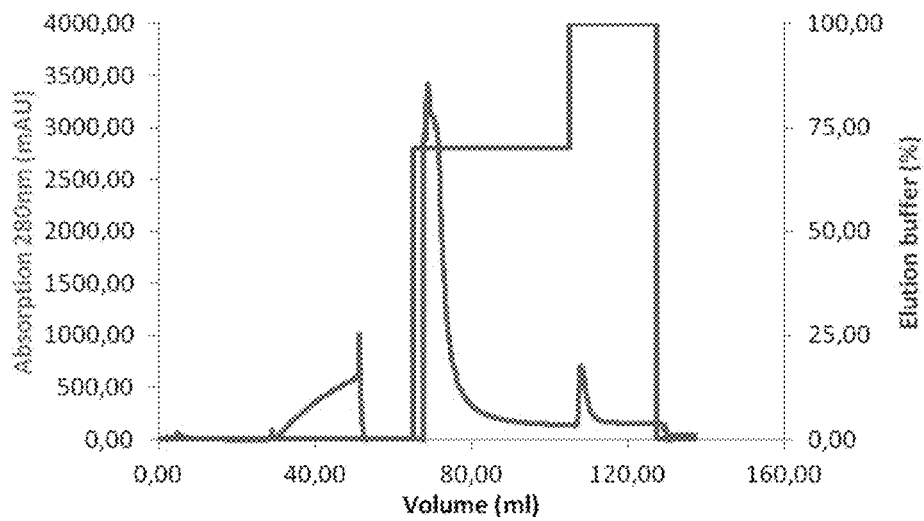
FIG. 13: Chromatogram of Insulin/aggregates purification with PP00446 at pH 3.5 using a step gradient and Dipropylene glycol in elution buffer.

For the following example 1 ml Polystyrene (PS) particles PP00446 are packed in a 10 mm diameter 6.2 long column using grinding beads for lengthening the column. For column packing 20% Ethanol 150 mM NaCl is prepared. The packed column is equilibrated using 50 mM Glycine/50 mM Acetic acid pH 3.5 (equilibration buffer) for 20 column volumes at 1 ml/min. The Insulin/aggregates solution is adjusted to pH 3.5 by adding acetic acid (insulin concentration: ~1.8 mg/ml). 50 ml of prepared solution is loaded on the equilibrated column at 1 ml/min while the flow through was collected in a flask. After accomplished loading the column is rinsed with equilibration buffer for 15 column volumes at 1 ml/min to wash out unbound Insulin. The flow through during the wash out step is collected in a second flask. Subsequently the elution is initialized using a step gradient (70% for 40 column volumes, 100% for 20 column volumes) using 50% Dipropylene glycol in 50 mM Glycine/50 mM Acetic acid as Elution buffer at 1 ml/min. The elutes are fractionated in 10 ml per fraction. FIG. 7 depicts the chromatogram recorded during the Insulin/aggregates purification. The collected fractions are subjected to non-reducing SDS-PAGE analysis (FIG. 13).

Figure 14:
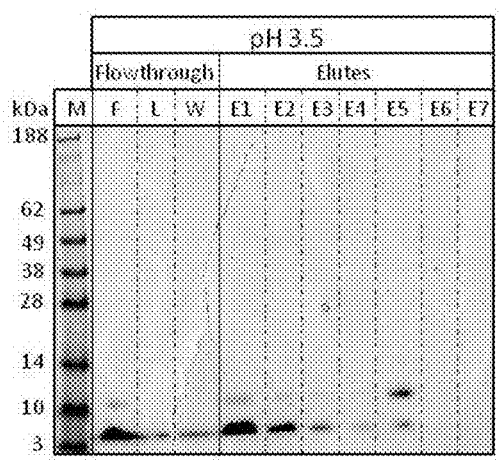
FIG. 14: Non-reducing SDS-PAGE analysis of all fractions during the Insulin/aggregates purification with PP00446 at pH 3.5 using a step gradient and Dipropylene glycol in elution buffer. Lanes: M—SeeBlue®Plus2 Prestained Standard, F—Feed Insulin starting material@pH 3.5, L—flowthrough collection during loading, W—flow through collection during wash step, elutes—elute fraction E1-E7 from P00446 column. Elution conditions: 50% DPG in 50 mM Glycine, 50 mM acetic acid pH 3.5.

As shown in FIG. 14 PP00446 resin bound Insulin and Insulin aggregates (dynamic binding capacity: >70 mg/ml). In this experiment the recovery achieved 96%. Moreover it is proven by the SDS-PAGE analysis that most Insulin aggregates are desorbed from the resin when the elution buffer concentration was higher than 70%. This property enables Insulin aggregate separation by applying an utilizable step gradient.

Example 10

In this experiment, particulate materials consisting of poly(ethyl)styrene (m) crosslinked with divinylbenzene (PS-DVB) copolymers is evaluated for its ability to remove aggregates from insulin at pH 8.0 using a step elution and dipropylen glycol.

Figure 15:
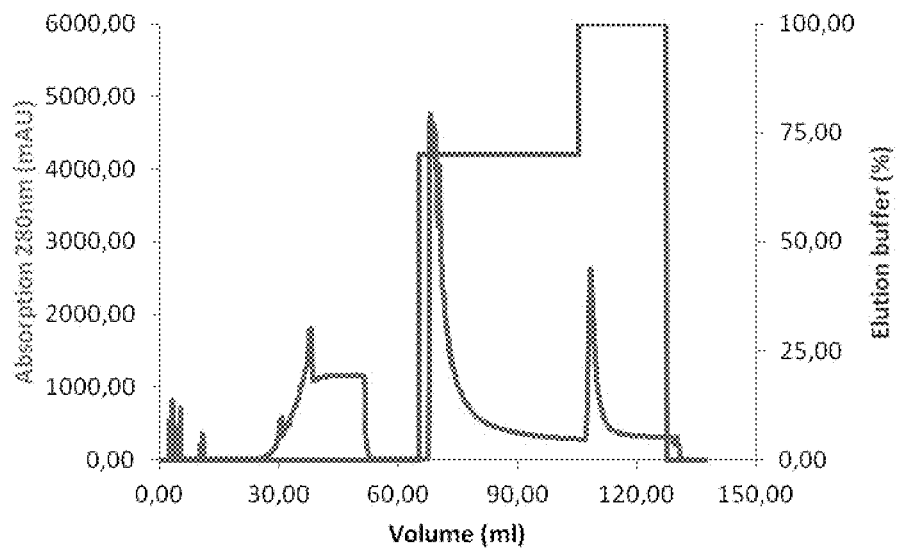
FIG. 15: Chromatogram of Insulin/aggregates purification with PRLP-S at pH 8.0 using a step gradient and Dipropylene glycol in elution buffer.

For the following example 1 ml Polystyrene (PS) particles PRLP-S are packed in a 10 mm diameter 6.2 long column using grinding beads for lengthening the column. For column packing 20% Ethanol 150 mM NaCl is prepared. The packed column is equilibrated using 50 mM TRIS pH 8.0 (equilibration buffer) for 20 column volumes at 1 ml/min. The Insulin/aggregates solution is adjusted to pH 8.0 by adding 1M TRIS. Furthermore the conductivity of the Insulin/aggregates solution is set to ~20 mS/cm by 1M NaCl solution (insulin concentration: ~1.6 mg/ml). 50 ml of prepared solution is loaded on the equilibrated column at 1 ml/min while the flow through is collected in a flask. After accomplished loading the column is rinsed with equilibration buffer for 15 column volumes at 1 ml/min to wash out unbound Insulin. The flow through during the wash out step is collected in a second flask. Subsequently the elution is initialized using a step gradient (70% for 40 column volumes, 100% for 20 column volumes) using 50% Dipropylene glycol in 50 mM TRIS pH 8.0 as elution buffer at 1 ml/min. The elutes are fractionated in 10 ml per fraction. FIG. 9 depicts the chromatogram recorded during the Insulin/aggregates purification. The collected fractions are subjected to non-reducing SDS-PAGE analysis (FIG. 15).

Figure 16:
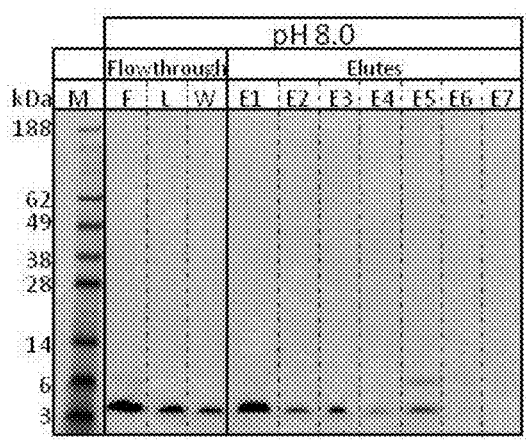
FIG. 16: Non-reducing SDS-PAGE analysis of all fractions during the Insulin/aggregates purification with PRLP-S at pH 8.0 using a step gradient and Dipropylene glycol in elution buffer. Lanes: M—SeeBlue®Plus2 Prestained Standard, F—Feed Insulin starting material@pH 8.0, L—flowthrough collection during loading, W—flow through collection during wash step, elutes—elute fraction E1-E7 from P00446 column. Elution conditions: 50% DPG in 50 mM TRIS pH 8.0.

As shown in FIG. 16 PRLP-S resin bound Insulin with a measured dynamic binding capacity >60 mg protein per ml packed bed. Furthermore the SDS-PAGE analysis outlines that solely Insulin monomers are desorbed from the resin with a elution buffer concentration of 70% (E1-E4). It is proven in FIG. 10 that Insulin aggregates are desorbed through the increase of the elution buffer to 100% (E5). The usage of a step elution gradient for Insulin aggregates separation streamlines the Insulin purification process.

Application of Polystyrene Particles for the Capture of Insulin

For the following example Polystyrene (PS) particles P00446 are used for capture of pure insulin (A11382IM, life technologies) in comparison to the common used LiChroprep® RP-18 (113900, Merck Millipore) beads and one cation exchange material (e.g. Eshmuno® S, 120078, Merck Millipore).

100 µl particles are washed with 1 ml of 50 mM Acetate pH 4. Afterwards 1 ml of a 5 mg/ml insulin solution in 50 mM Acetate pH 4 is adsorbed for 30 minutes at 25° C. After centrifugation the supernatant is removed (5 µl are mixed with 5 µl gel loading buffer, NP0007, life technologies). Particles are washed with 1 ml 50 mM Acetate pH 4 and split in 2 tubes. After centrifugation the supernatant is discarded. For beads after adsorption one part of the particles are resuspended in 500 µl gel loading buffer. The other part is eluted with 500 µl of 50 mM Acetate, 40 Vol % DPG, pH 4 respectively 50 mM phosphate, 500 mM NaCl, pH 8 for Eshmuno® S for 30 minutes at 25° C. After centrifugation the supernatant is removed (5 µl were mixed with 5 µl gel loading buffer). Particles are washed with 500 µl 50 mM Acetate pH 4. After centrifugation the supernatant is discarded. For beads after elution the particles are resuspended in 500 µl gel loading buffer. After heating all samples for 10 minutes at 99° C. 10 µl of supernatant/eluate respectively 5 µl of bead-samples are loaded on 4-12% NuPAGE® Novex® Bis-Tris Gel (NP0336, life technologies). Gel is run for 25 minutes at 200 V constant. After washing with pure water it is stained with SimplyBlue™ SafeStain (LC6065, life technologies) and destained with pure water. FIG. 1 shows a non-reducing SDS-PAGE of static capture insulin on P00446, LiChroprep® RP-18 and Eshmuno® S.

Conditions:

A mixture of 1 ml of 5 mg/ml insulin and 50 mM Acetate pH 4 is added to 100 µl equilibrated particles. Adsorption is carried out for 30 minutes at a temperature of 25° C. Subsequently elution is done for 30 minutes at a temperature of 25° C. with 500 µl 50 mM Acetate and 40 Vol % DPG, pH 4 respectively 50 mM phosphate, 500 mM NaCl, pH 8 for
Eshmuno® S.

Lanes: M . . . MW-Marker
S . . . Start material
SA . . . supernatant after adsorption
BA . . . beads after adsorption
E . . . Eluate
BE . . . beads after elution As shown in
FIG. 1 the polystyrene beads P00446 adsorb insulin nearly complete which correspond to a static binding capacity of 50 mg protein per ml particle-suspension. 40 Vol % Dipropylene glycol is a useful desorption solution. The new technology of PS particles is comparable to the common used cation exchange process.

In comparison LiChroprep® RP-18 (as an alternative reverse phase material) does not adsorb insulin under the given conditions.

Application of Polystyrene Particles for the Capture of Crude Insulin A

For the following example Polystyrene (PS) particles P00446 are packed in a 10 mm diameter 12 mm long column using 20% ethanol 150 mM NaCl solution.

The packed column is equilibrated using 50 mM Glycine/50 mM Acetic acid buffer pH 3.5 for at least 20 column volumes at 1 ml/min. The crude insulin solution A is adjusted to pH 3.5 (insulin concentration-1.7 g/L). 60 ml of obtained solution is directly loaded on the equilibrated column at 1 ml/min and the flow through fraction is collected in a separate flask. After loading, the column is washed with 10CV using equilibration solution. The elution of the captured crude insulin is performed using a gradient elution from 0-100% of 50% ethanol in 50 mM Glycine/50 mM Acetic acid buffer pH 3.5 in 30 CV at 1 ml/min (FIG. 2). The fractions are collected and subjected to non-reducing SDS-PAGE analysis (FIG. 3).

FIG. 2 shows the elution peak of the captured crude insulin from P00446 polystyrene particles.

FIG. 3 shows a non-reducing SDS-PAGE of dynamic crude insulin capture on P00446.

As shown in FIG. 3 the polystyrene beads P00446 adsorb insulin nearly complete which correspond to a binding capacity of >80 mg protein per ml packed bed. 50 Vol % ethanol is a useful desorption solution (e.g. recovery 101.33%), enabling to use polystyrene particles for aggregate and target molecule separation, that is not noticed using ion exchangers for the crude insulin capture (data not shown).

Application of Polystyrene Particles for the Capture of Crude Insulin B

For the following example Polystyrene (PS) particles P00446 are packed in a 10 mm diameter 12 mm long column using 20% ethanol 150 mM NaCl solution.

The packed column is equilibrated using 50 mM TRIS, 100 mM Arginine buffer pH 7.0 for at least 20 column volumes at 1 ml/min. The crude insulin solution B originating from E. coli expression system is adjusted to pH 3.5 and 30 ml of obtained solution is directly loaded on the equilibrated column at 1 ml/min and the flow through fraction collected in a separate flask. After loading, column is washed with 10CV using equilibration solution. The elution of the captured crude insulin is performed using a gradient elution from 0-100% of 60% dipropylenglycol in 50 mM Glycine/50 mM Acetic acid buffer pH 3.5 in 20 CV at 1 ml/min. The fractions are collected and subjected to non-reducing SDS-PAGE analysis (FIG. 4).

FIG. 4 shows a non-reducing SDS-PAGE of dynamic capture raw insulin on P00446 (Column 1.1 ml diameter 10 mm) using ÄKTA FPLC system. 10 CV Equillibration with 25 mM Tris, 100 mM Arginine, pH 7. 30 ml of 1 mg/ml raw insulin are loaded with 1 ml/min flowrate. Elution in 20 CV from 0% till 100% 60 Vol. % DPG.

Lanes: M . . . MW-Marker
S . . . Start material
FT . . . Flow Through

As shown in FIG. 4 the polystyrene beads P00446 adsorb insulin (5% purity) from the crude solution and dipropylenglycol solution can be applied to separate insulin fragments from aggregates and target achieving >40% purity.

Application of Polystyrene Particles for the Capture of Crude Protein pSCP194

For the following example Polystyrene (PS) particles P00446 are packed in a 10 mm diameter 12 mm long column using 20% ethanol 150 mM NaCl solution.

The packed column is equilibrated using 50 mM TRIS, 100 mM Arginine buffer pH 7.0 for at least 20 column volumes at 1 ml/min. The crude E. coli lysate containing protein pSCP194 is adjusted to pH 7.0 and 20 ml of obtained solution is directly loaded on the equilibrated column at 1 ml/min and the flow through fraction collected in a separate flask. After loading, the column is washed with 10CV using equilibration solution. The elution of the captured crude insulin is performed using a gradient elution from 0-100% of 60% dipropylenglycol in 50 mM Glycine/50 mM Acetic acid buffer pH 3.5 in 20 CV at 1 ml/min. The fractions are collected and subjected to non-reducing SDS-PAGE analysis (FIG. 5).

FIG. 5 shows a non-reducing SDS-PAGE of dynamic crude pSCP194 capture on P00446 (Column 1.1 ml diameter 10 mm).

As shown in FIG. 5 the polystyrene beads P00446 adsorb pSCP194 protein from the crude *e. coli* lysate solution and dipropylenglycol solution can be applied to elute the captured target achieving >80% purity.

Application of Polystyrene Particles for the Capture of Crude Insulin in Urea

For the following example Polystyrene (PS) particles P00446 are packed in a 10 mm diameter 12 mm long column using 20% ethanol 150 mM NaCl solution.

The packed column is equilibrated using 50 mM Glycine/50 mM acetic acid buffer pH 3.5 for at least 20 column volumes at 1 ml/min. The crude insulin solution containing aggregated insulin after incubation in 8M urea solution is diluted to 2M urea concentration using pure water adjusted to pH 3.5. 50 ml of obtained solution was directly loaded on the equilibrated column at 1 ml/min and the flow through fraction collected in a separate flask. After loading, column is washed with 10CV using equilibration solution. The elution of the captured crude insulin is performed using a gradient elution from 0-100% of 60% dipropylenglycol in 50 mM Glycine/50 mM Acetic acid buffer pH 3.5 in 20 CV at 1 ml/min. The fractions are collected and subjected to non-reducing SDS-PAGE analysis (FIG. 6). FIG. 6: shows a non-reducing SDS-PAGE of dynamic crude insulin capture on P00446 and PS02 (Column 1.1 ml diameter 10 mm).

As shown in FIG. 6 the polystyrene beads P00446 and PS02 adsorb insulin from the crude 2M urea containing solution and dipropylenglycol solution can be applied to elute the captured target achieving >90% purity (fractions A3-A4 and A11-A12).

What is claimed:

1. A method for separating peptide aggregates and fragments from solutions containing the target peptide, comprising the steps of
   (a) providing the sample containing the target peptide;
   (b) contacting the sample with a hydrophobic chromatography material
      for a suitable period of time and adsorbing peptides comprising the target peptide and optionally peptide aggregates and fragments in the sample, and wherein the hydrophobic chromatography material, is particulate, which is made of cross-linked polymer, selected from the group consisting of ethylstyrene, poly(ethyl)styrene-divinylbenzene, and poly(ethyl) styrene-divinylbenzene ethyleneglycol-dimethylacrylate resin and wherein the particulate hydrophobic chromatography material is a resin, which is composed of a cross-linked polymer consisting of styrene and divinylbenzene in a ratio 98:2 up to 10:90% by weight or of polystyrene, which is cross-linked with copolymer of divinylbenzene and ethylenglycoldi-methacrylate in a ratio of 98:2 up to 10:90% by weight,
   (c) recovering the target peptide from the hydrophobic chromatography material by use of different solvent compositions and thereby separating aggregated peptides and peptide fragments from the target peptide and wherein organic solvents selected from the group consisting of ethanol, 1-propanol and dipropylenglycol are used in the different solvent composition to selectively desorb the adsorbed peptides from the hydrophobic chromatography material;
      wherein the separation of peptide aggregates is processed after a target molecule refolding step and,
      wherein after contacting the sample with a hydrophobic chromatography material for a suitable period of time and adsorbing the peptides, the loaded chromatography material is subjected to post peptide refolding solutions for selectively reducing the level of aggregated substances for a suitable period of time, and
      wherein in step b) the hydrophobic chromatographic materiel is exposed to 30-100 mg of target peptide per ml of packed bed, at a flow rate in the range of 150-1000 cm/min.

2. A method according to claim 1, wherein the particulate hydrophobic chromatographic separation material has mean particle diameters in the range of 10 μm to 600 μm.

3. A method according to claim 1, wherein the particulate hydrophobic chromatographic separation material consists of hydrophobic porous polymer beads having pore sizes in the range of 4-500 nm.

4. A method according to claim 1, wherein in step b) an aqueous solution containing the target peptide, having a pH value in the range of 2-11, and a conductivity in the range of 1-150 mS/cm, is contacted with a hydrophobic chromatography material.

5. A method according to claim 1, wherein in step c) the hydrophobic chromatographic material is exposed to an aqueous solution comprising organic solvent in direct or gradient manner, whereby depending on the concentration of the contained organic solvent, separation of the aggregated peptides and peptide fragments from the target peptide is achieved.

6. A method according to claim 1, wherein in step c) a selective desorption and separation of the bound components is achieved using various ratios of organic solvents contained in an aqueous mixture.

7. A method according to claim 1, wherein the separation and purification sequence includes a treatment with an ion exchange resin.

8. A method according to claim 1, wherein the separation and purification is carried out in a bind and elute mode, whereby the flow velocity is adjusted in the range of 150 cm/min-1000 cm/min.

9. A method according to claim 1, wherein in step b) the sample is contacted with a hydrophobic chromatography material in form of polymer beads in a liquid chromatography column having a diameter ranging from 1 to 100 cm, and where the column is operated at pressures up to 100 bar.

10. A method according to claim 1, wherein the sample is contacted with a hydrophobic chromatography material in form of polymer beads in a liquid chromatography column having a diameter in the range of 10 to 50 cm and where the column is operated at pressures in the range of 0.2 to 80 bar.

11. A method according to claim 1, wherein in step a) a crude insulin solution originating from *E. coli* expression system is provided.

12. The method according to claim 3, wherein the hydrophobic porous polymer beads have a pore size in the range of 10-30 nm.

13. The method according to claim 3, wherein the hydrophobic porous polymer beads have a pore size the range of 13 nm to 25 nm.

14. The method according to claim 4, wherein the aqueous solution containing the target peptide has a pH value in the range of 3-8 and a conductivity in the range 2-50 mS/cm.

15. The method according to claim 1, wherein in step b) the hydrophobic chromatographic material is exposed to 50-80 mg of target peptide per ml of packed bed at a flow rate in the range of 300-900 cm/min.

16. The method according to claim 8, whereby the flow velocity is adjusted in the range of 300-900 cm/min.

17. The method according to claim 9, wherein the liquid chromatography column has a diameter ranging from 5 to 50 cm, and where the column is operated at a pressure of 0.2 to 80 bar.

18. The method according to claim 2, wherein the particulate hydrophobic chromatographic separation material has mean particle diameters in the range of 20 μm to 150 μm.

19. The method according to claim 2, wherein the particulate hydrophobic chromatographic separation material has mean particle diameters in the range of 20 μm to 63 μm.

* * * * *